US008226685B2

(12) United States Patent
Lederman et al.

(10) Patent No.: US 8,226,685 B2

(45) Date of Patent: Jul. 24, 2012

(54) SUTURE ANCHOR AND METHOD OF USE

(75) Inventors: Evan Lederman, Paradise Valley, AZ (US); Dick Winiker, Tempe, AZ (US); Laird Hatch, Cave Creek, AZ (US)

(73) Assignee: Redline Orthopedic Innovations, LLC, Tempe, AZ (US)

( * ) Notice: Subject to any disclaimer, the term of this patent is extended or adjusted under 35 U.S.C. 154(b) by 393 days.

(21) Appl. No.: 12/547,309

(22) Filed: Aug. 25, 2009

(65) Prior Publication Data

US 2011/0054525 A1 Mar. 3, 2011

(51) Int. Cl.
*A61B 17/00* (2006.01)

(52) U.S. Cl. ........................................................ 606/232

(58) Field of Classification Search .................. 606/232, 606/139, 144; 128/898

See application file for complete search history.

(56) References Cited

U.S. PATENT DOCUMENTS 5,207,679 A 5/1993 Li
5,224,946 A 7/1993 Hayhurst et al.
5,324,308 A * 6/1994 Pierce ............................ 606/232
5,403,348 A * 4/1995 Bonutti .......................... 606/232
5,405,359 A * 4/1995 Pierce ............................ 606/232
5,531,759 A * 7/1996 Kensey et al. ................ 606/213
5,549,630 A * 8/1996 Bonutti .......................... 606/232
5,645,588 A 7/1997 Graf et al.
5,810,884 A * 9/1998 Kim .............................. 606/213
5,845,645 A * 12/1998 Bonutti ......................... 128/898
6,117,161 A * 9/2000 Li et al. ......................... 606/232
6,287,325 B1 * 9/2001 Bonutti ......................... 606/232
6,592,609 B1 * 7/2003 Bonutti ......................... 606/232
6,843,799 B2 1/2005 Bartlett
6,887,259 B2 5/2005 Lizardi
7,481,825 B2 * 1/2009 Bonutti ......................... 606/216
7,686,838 B2 * 3/2010 Wolf et al. ..................... 606/325
7,846,180 B2 * 12/2010 Cerier ........................... 606/232
7,850,714 B2 * 12/2010 Rotella et al. ................. 606/232
2004/0097939 A1 * 5/2004 Bonutti ........................... 606/69
2004/0133238 A1 * 7/2004 Cerier ........................... 606/232
2004/0225325 A1 * 11/2004 Bonutti ......................... 606/232
2005/0055052 A1 * 3/2005 Lombardo et al. ............ 606/232

OTHER PUBLICATIONS

International Search Report and Written Opinion regarding PCT/US2010/046579, dated Nov. 29, 2010.

* cited by examiner

*Primary Examiner* — Corrine M McDermott

*Assistant Examiner* — Todd J Scherbel

(74) *Attorney, Agent, or Firm* — Meschkow & Gresham, P.L.C.

(57) ABSTRACT

A suture anchor 20 is inserted within the spongy bone 22" such that only suture segments 40 and 42 extend into the cortical bone 22'. Suture anchor 20 is inserted with a suture inserting device 58 that holds suture anchor 20 until suture inserting device 58 has entered spongy bone 22". Deployment device 62 pushes suture anchor 20 from suture inserting device 58 into spongy bone 22". Suture anchor 20 is positioned such that suture anchor 20 spans the hole 24 through which suture inserting device 58 inserted suture anchor 20.

5 Claims, 3 Drawing Sheets

40 42 104 36 38 110 34 94 96 108 98 106

114 96 94 112 36 38 34 98

30

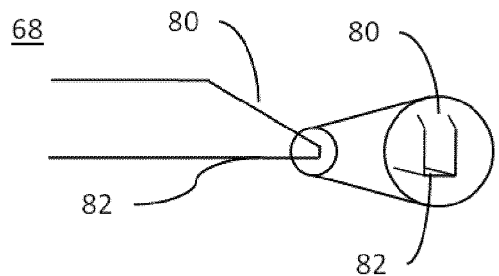
FIG. 4
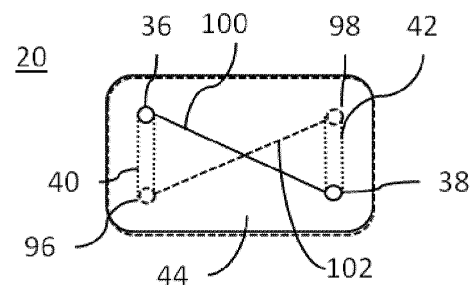
FIG. 6
FIG. 5
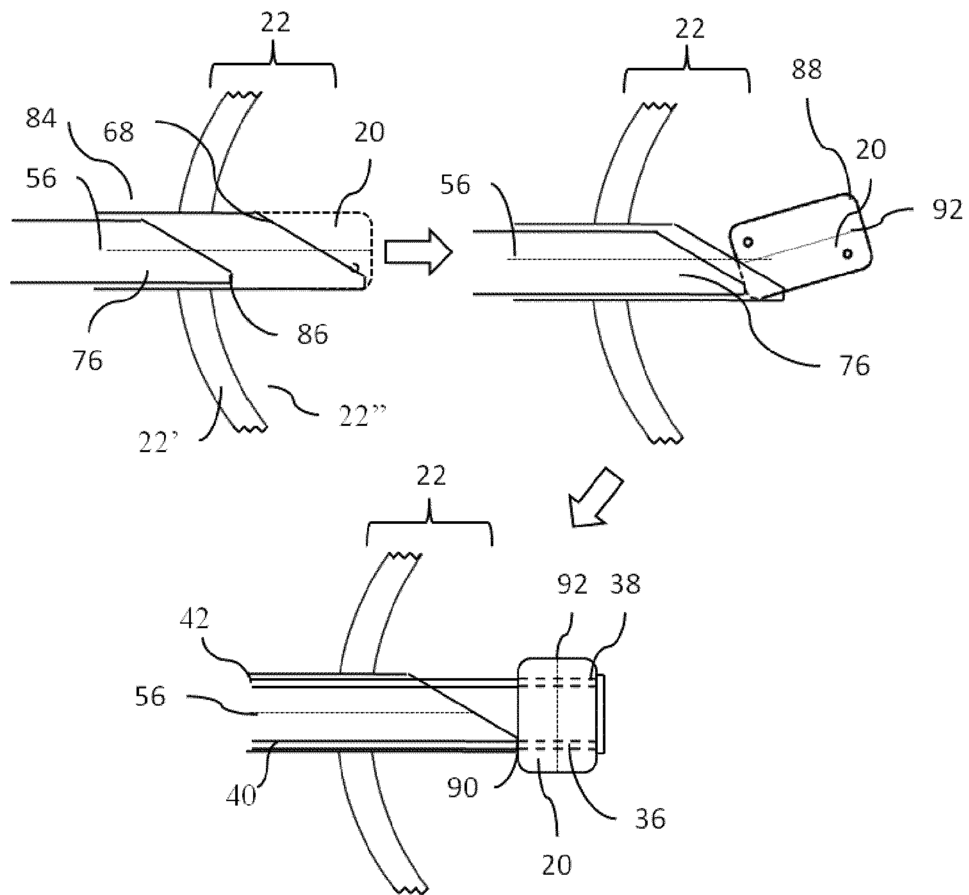

SUTURE ANCHOR AND METHOD OF USE

TECHNICAL FIELD OF THE INVENTION

The present invention relates to the field of securing soft tissue within a patient. More specifically, the present invention relates to securing a soft tissue to a bone.

BACKGROUND OF THE INVENTION

The advantages of a minimally invasive procedure, such as arthroscopy, as opposed to an open surgery, include less trauma to the patient, faster recovery time, shorter stays in expensive medical facilities, to name but a few. As a result, the use of these types of procedures has increased. Minimally invasive surgical procedures require the use of instruments that can be positioned and placed within the body through a small incision, requiring high precision while also being easy to maneuver and use. Among the many procedures performed using such minimally invasive procedures include the treatment of injuries such as torn cartilage or ligaments, requiring the fixation of soft tissue to bone for proper healing.

Traditionally, in order to ensure that the sutures used will be able to secure the soft tissue to the bone, surgeons have used suture anchors that affix to the bone, thus securing a portion of the suture to the bone. This is done to increase the likelihood that the soft tissue will reattach itself to the bone surface, rather than being pulled away. In order to use these conventional devices, the surgeon will make a hole in the cortical bone, and insert the suture anchor within the hole. The anchor is designed to secure itself within the cortical bone by exerting some pressure on the cortical bone surface, digging into the bone itself, or any other method that ensures that the anchor cannot be easily extracted from the bone. After the anchor is secured, surgeons use the suture that is attached to the anchor to affix the soft tissue to the bone.

Unfortunately, the level of growth of the soft tissue onto the bone may be limited when using these devices. Some devices are designed so that a large portion of the anchor is within the cortical bone; however a portion of the anchor, along with the suture, sits outside the surface of the cortical bone. The protruding surface will often have contact with the soft tissue that is being sutured to the cortical bone. The irritation caused by the anchor on the soft tissue may prolong, if not hinder, full recovery from the surgical procedure.

Other conventional devices place the entire body of the suture anchor within the hole made in the cortical bone such that the no portion of the device extends beyond the outer surface of the cortical bone into the soft tissue, or beyond the inner surface of the cortical bone into the spongy bone. These suture anchors are placed under stress, as the sutures are pulled from the anchor to the outer surface of the bone. At times, this stress can cause the suture anchor to move, possibly resulting in a portion of the anchor ultimately protruding from the outside surface of the cortical bone, thus causing problems similar to those discussed earlier. Also, such movement of the anchor within the bone further increases the damage that is done to the cortical bone, and increases the likelihood that further treatment will be necessary to correct the injury.

The cortical bone is also capable of mending itself whenever it is damaged. However, similar to the soft tissue surrounding it, the cortical bone must be free from irritations or obstructions to heal quickly and properly. When conventional surgical anchors occupy an opening through the cortical bone, these devices can be causes for irritation, although the bone may grow around the anchor. This may result in increasing the time to full recovery, if not preventing full recovery all together.

Many times, individuals who undergo arthroscopies reinjure themselves in the same joints or other locations. As a result, oftentimes the same arthroscopic procedure must be done multiple times in the same area. Although the bone may heal itself, due to the method of installing these bone anchors, once one is in place, it cannot be removed without incurring further damage to the bone. As a result, if further injury is suffered at the same site, or in a close vicinity to the site where the suture anchor was installed, the previously installed suture anchor cannot be moved to make room for a new one. This reduces the options that are available to the patient for repairing the injuries they suffer.

There are some suture anchor devices that are not designed to occupy a hole through the cortical bone, but rather are designed to pass through the center of the bone, and come out to the other side. Because the anchor is not sitting within the bone itself, the need for small devices is not as much of a concern. By using the distal outer surface of the bone to support the sutures, the need to ensure that the suture anchor is well secured within the bone becomes unnecessary. However, in order to install these devices, it is necessary for the surgeon to drill through both sides of a bone, and then pass this device through the bone to the other side. This maneuver is difficult, if not impossible, in minimally invasive surgeries, such as arthroscopies, as the device must be threaded through the bone and pulled out the other side.

Although this type of anchor does reduce if not nullify the irritation concerns that arise with other conventional suture anchors, the amount of trauma that the installation does to an individual's body is great. There is significant trauma to the bone, as it is necessary to drill through the cortical bone on the side where the device will enter the bone, through the spongy bone, and through the cortical bone on the opposite side where the device will exit the bone. This trauma is further increased by by installing the device after the extensive hole-drilling operations are complete.

In order to install this anchor, the surgeon would have to pass one end of the anchor through the hole, grab the anchor on the other side of the bone, and properly position the device. This sort of device cannot be used in surgeries that are done in very small areas where the opposing side of the bone is not readily visible or accessible during a surgery. Also, in surgeries performed on bones that abut nerves, it would be virtually impossible for the surgeon to install this device without increasing the likelihood of serious injury to the patient. Furthermore, there is much more internal area of the bone that is exposed when this device is used. Unlike in the conventional suture anchors discussed above, this device will leave at least one hole in the bone that is not covered, and exposes the interior spongy bone to the outside. This provides more opportunity for complications from infection to arise.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, and:

FIG. 4 shows a profile view of a suture anchor holder in accordance with a preferred embodiment of the present invention;

FIG. 5 shows an exploded view of a suture anchor system in accordance with a preferred embodiment of the present invention;

FIG. 6 shows a top-view depicting a suture anchor prior to deployment in accordance with an alternative preferred embodiment of the present invention;

DETAILED DESCRIPTION OF THE PREFERRED EMBODIMENTS

Figure 1:
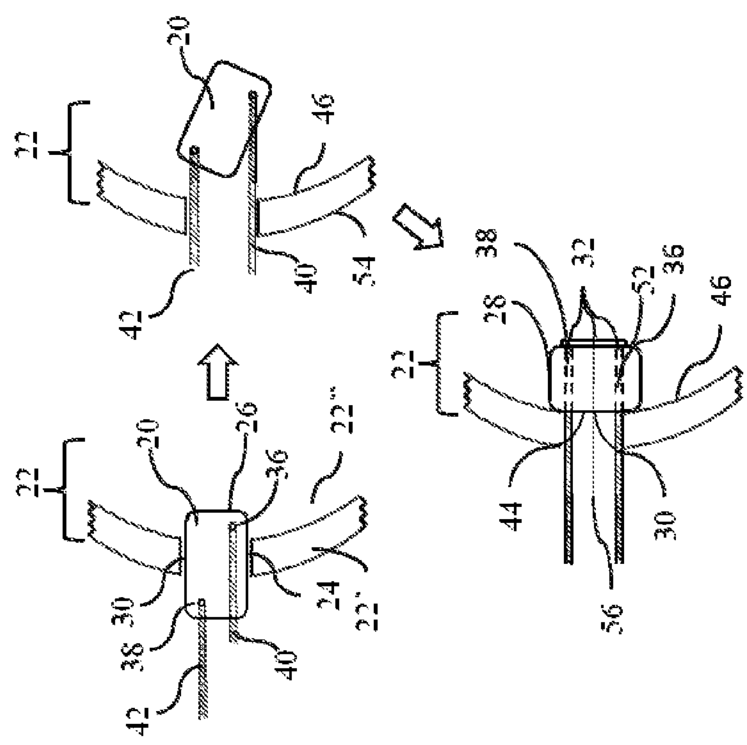
FIG. 1 shows a suture anchor as it is inserted into a bone in accordance with a preferred embodiment of the present invention.

FIG. 1 shows a suture anchor 20 as it is inserted into a bone 22. Suture anchor 20 is designed to be inserted into bone 22 during minimally invasive surgical procedures. In those situations, the amount of space available for the devices to be positioned is minimal. Suture anchor 20 is inserted through a hole 24 in cortical bone 22'. In one embodiment, hole 24 is made prior to suture anchor 20 being inserted. In another embodiment, suture anchor 20 creates hole 24 as it is inserted through cortical bone 22'. In the embodiment that suture anchor 20 creates hole 24, suture anchor 20 will have an end that is tapered to a point (not shown), which is configured to aid in creating hole 24 for suture anchor 20. Suture anchor 20 includes a height 26, width 28, and length 30. Length 30 is greater than both height 26 and width 28.

Figure 2:
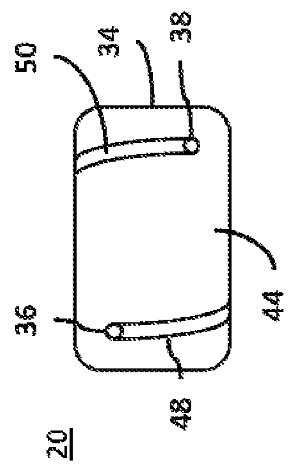
FIG. 2 shows top-view of a suture anchor in accordance with a preferred embodiment of the present invention.

FIG. 2 is a top-view of suture anchor 20. Suture anchor 20 is used to provide an anchor against which a suture 32 (FIG. 1) can be braced to while suturing soft tissue to a bone 22 (FIG. 1). In order to facilitate this, suture anchor 20 includes a sterile anchor segment 34 having a first hole 36 and a second hole 38. There is always a chance that a body may become exposed to a viral or bacterial infection. As an attempt to reduce this chance, operations are done in clean operation theaters, and individuals in the operating theaters go through extensive scrubbing procedures. Similarly, medical devices, such as anchor segment 34, that are used in surgical procedures are sterilized to ensure that the chances of infection when used in a patient's body are reduced. In one embodiment, sterile anchor segment 34 has rounded corners so as to reduce irritation inside bone 22 when suture anchor 20 is used. When suture anchor 20 is deployed, sterile anchor segment 34 rotates within bone 22 (discussed below). During this rotation, sharp corners on sterile anchor segment 34 may cause sterile anchor segment 34 to tear or otherwise damage the interior of bone 22. First hole 36 and second hole 38 extend through height of sterile anchor segment 34, and are configured to permit suture 32 to pass through from one side of suture anchor 20 to the other. A first suture segment 40 (FIG. 1) passes through first hole 36 and a second suture segment 42 (FIG. 1) passes through second hole 38. In one embodiment, suture anchor 20 is used as part of a knotless system, in which first suture segment 40 and second suture segment 42 are part of a single, integrated suture 32. In another embodiment, suture anchor 20 is used as part of a knotted system, where first suture segment 40 and second suture segment 42 are knotted together (not shown) on one side of suture anchor 20.

While providing an anchor for suture 32, a top surface 44 of suture anchor 20 is proximal to the inner surface 46 of a bone 22. In one embodiment top surface 44 has a contour that is similar to that that of the inner surface 46 (FIG. 1) of cortical bone 22' (FIG. 1). To facilitate the flow of fluids from a spongy bone 22" (FIG. 1) to cortical bone 22' in the area occupied by suture anchor 20, at least a first groove 48 and a second groove 50 may be etched or otherwise formed into top surface 44. Permitting fluid flow in this way speeds the healing and regrowth process of cortical bone 22'.

Suture 32 is threaded through suture anchor 20 such that first suture segment 40 passes through first hole 36 and second suture segment 42 passes through second hole 38. First suture segment 40 and second suture segment 42 join at a back side 52 (FIG. 1) of suture anchor 20, and first and second suture segments 40 and 42 are available to place sutures proximal to an outer surface 54 of cortical bone 22'. When suture anchor 20 is inserted into bone 22, first hole 36 in anchor 20 will enter hole 24 in bone 22 before second hole 38 in anchor 20.

Returning to FIG. 1, after suture anchor 20 is fully inserted into bone 22, tension is applied to first suture segment 40, so that a side of suture anchor 20 proximal to first hole 30 is pulled towards inner surface 46 of cortical bone 22'. This will cause suture anchor 20 to rotate from an axis 56 aligned with the direction of movement through the hole 24, span hole 24, and thus provide an anchor for any sutures that may be placed in the soft tissue. After suture anchor 20 is inserted, it cannot be extracted from hole 24 without properly aligning suture anchor 20 which cannot be done without additional maneuvering of suture anchor 20. In one embodiment, rounded corners for sterile anchor segment 34 may also help the rotation that is needed to properly position suture anchor 20 by making it less likely that suture anchor 20 will bind up during deployment but will rotate in two dimensions to span hole 24 even when the corners of suture anchor 20 contact structures in bone 22.

When minimally invasive surgical procedures are used in concert with suture anchor 20, it may be difficult to insert and position suture anchor 20, as such procedures are conducted through small incisions in the patient. To aid in the insertion, deployment and positioning of suture anchor 20, a suture anchor inserting device may be used.

Figure 3:
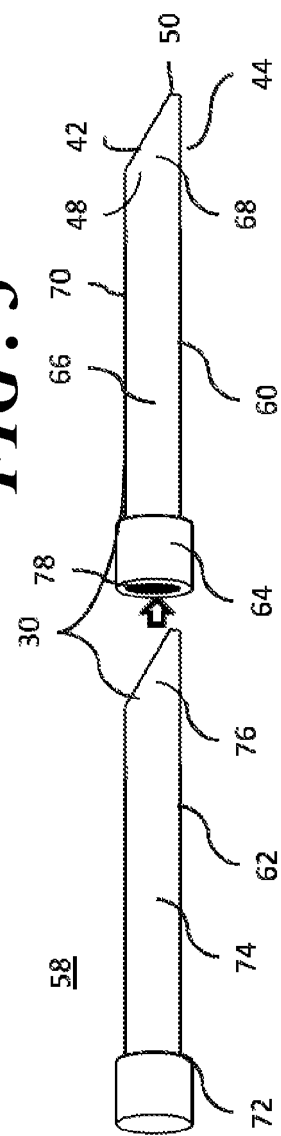
FIG. 3 shows a suture anchor inserting device in accordance with a preferred embodiment of the present invention.

FIG. 3 shows a suture anchor inserting device 58. Suture anchor inserting device 58 has a positioning unit 60 and a deployment device 62. Although FIG. 3 depicts deployment device 62 removed from positioning unit 60, during use deployment device 62 may be inserted into positioning unit 60 and move laterally within positioning unit 60 under the control of a human or mechanical operator. Positioning unit 60 is configured to hold suture anchor 20 during insertion of suture anchor 20 into bone 22, and to position suture anchor 20 within bone 22 prior to deployment. Once suture anchor 20 is deployed, positioning unit 60 also may be used to position suture anchor 20 such that suture anchor 20 spans hole 24. Deployment device 62 is configured to deploy suture anchor 20. Deployment device 62 does this by pushing suture anchor 20 from positioning unit 60 once positioning unit 60has been inserted into bone 22.

Positioning unit 60 includes a positioning handle 64, a positioning shaft 66 and a suture anchor holder 68. Suture anchor holder 68 is configured to hold suture anchor 20 prior to deployment in bone 22. Suture anchor holder 68 is affixed to positioning shaft 66. Positioning shaft 66 has a length 70 such that when positioning unit 60 is used, positioning shaft 66 will extend from the interior of bone 22 to outside a patient's body. Positioning handle 64 is affixed to positioning shaft 66 at an end distal from suture anchor holder 68. Positioning handle 64 is configured to permit a user of suture inserting device 58 to position suture anchor holder 68 within bone 22 from outside a patient's body.

Deployment device 62 includes a deployment handle 72, a deployment shaft 74 and a deployment end 76. Deployment end 76 is configured to push suture anchor 20 from suture anchor holder 68. When deployment end 76 pushes suture anchor 20, it encourages a rotation of suture anchor 20 from axis 56 (FIG. 1) aligned with the direction of movement through hole 24. (discussed below). Deployment shaft 74 has a length which is at least equal to the length of positioning shaft 66 such that deployment end 76 will be able to touch and push suture anchor 20 out of suture anchor holder 68. Affixed to deployment shaft 74, distal from deployment end 76, deployment handle 72 is configured to permit a user of suture inserting device 58 to apply pressure and push suture anchor 20 (FIG. 2) from suture anchor holder 68.

Positioning handle 64 and positioning shaft 66 have a hole 78 configured to accept deployment device 62. To deploy suture anchor 20 from suture anchor holder 68, deployment end 76 is placed in hole 78 at positioning handle 64, and deployment device 62 is pushed into positioning unit 60 such that deployment end 76 travels the length of positioning shaft 66 and reaches suture anchor holder 68 (discussed below).

FIG. 4 is a profile view of suture anchor holder 68. Suture anchor holder 68 holds suture anchor 20 (FIG. 2) such that it cannot become dislodged until it is pushed out by deployment device 62 (FIG. 3). In one embodiment, suture anchor holder 68 uses frictional forces to hold suture anchor 20. In another embodiment, a flap (not shown), closed by deployment end 76 (FIG. 3) approaching suture anchor holder 68, prevents suture anchor 20 from being released from positioning unit 60.

Suture anchor holder 68 is configured to permit suture anchor 20 to rotate from axis 56 (FIG. 1) as suture anchor 20 is released from suture anchor holder 68. To facilitate this, in one embodiment, suture anchor holder 68 has an open side 80 and a closed side 82. When examining the cross-sectional view of suture anchor holder 68, open side 80 is not covered, resulting in suture anchor holder 68 having a substantially "U" shaped cross-section.

In one embodiment, when suture anchor 20 is held in suture anchor holder 68, grooves 48 and 50 (FIG. 2) are able to accept first suture segment 40 and second suture segment 42, so that first suture segment 40 and second suture segment 42 do not intertwine or otherwise become damaged or tangled during insertion and deployment.

FIG. 5 shows suture anchor system 84 as it deploys suture anchor 20 within bone 22. Suture anchor system 84 includes suture anchor inserting device 58 (FIG. 3) and suture anchor 20 held within suture anchor holder 68. Suture anchor 20 is placed within suture anchor inserting device 58 prior to inserting suture anchor inserting device 58 within bone 22. To insert suture anchor 20 into bone 22, hole 24 is formed through cortical bone 22' from outside bone 22 to spongy bone 22". It is not necessary to form hole 24 through both sides of bone 22, as this is unnecessary trauma that is placed on bone 22. Hole 24 has a width greater than width 28 (FIG. 2) of suture anchor 20 and a height less than height 26 (FIG. 2) of suture anchor 20 so that suture anchor 20 may enter hole 24.

FIG. 5 shows suture anchor holder 68 of suture anchor system 84 holding suture anchor 20, and deployment device 62 deploying suture anchor 20. Prior to deployment suture anchor system 84 is inserted into bone 22 such that suture anchor holder 68 is within spongy bone 22". When suture anchor holder 68 is within spongy bone 22", suture anchor 20 is also within spongy bone 22". Thus, when deployed, suture anchor 20 will not be caught within cortical bone 22', but rather will sit within spongy bone 22". When suture anchor holder 68 has been positioned, deployment device 62 is inserted within positioning unit 60, if it has not already been positioned there. Deployment end 76 comes in contact with suture anchor 20 at a point 86 and pushes suture anchor 20 from suture anchor holder 68. Suture anchor 20 then rotates from axis 56 aligned with the direction of motion of positioning unit 60 through hole 24. To encourage this rotation, in one embodiment, point 86 is off-center from suture anchor 20. By positioning point 86 proximal to closed side 82, suture anchor 20 can be encouraged to rotate at open side 80, such that a leading edge 88 rotates out of suture anchor holder 68.

In one embodiment, positioning unit 60 may also be used to align suture anchor 20 such that suture anchor 20 spans hole 24 prior to removing positioning unit 60. In this embodiment, after suture anchor 20 is deployed using deployment device 62, first suture segment 40 is pulled so that a side of suture anchor 20 proximal to first hole 36 is pulled towards positioning handle 64. This will cause suture anchor 20 to further rotate from axis 56. Second suture segment 42 is also pulled, so that top surface 44 (FIG. 2) of suture anchor 20 touches an edge 90 of suture anchor holder 68. In one embodiment, when top surface 44 of suture anchor 20 touches edge 90, suture anchor 20 axis 92 is perpendicular to axis 56.

After suture anchor 20 is thus aligned, suture anchor inserting device 58 is extracted from hole 24 and suture anchor 20 spans hole 24. First suture segment 40 and second suture segment 42 extend from outside hole 24 to inside spongy bone 22" through hole 24.

Figure 7:
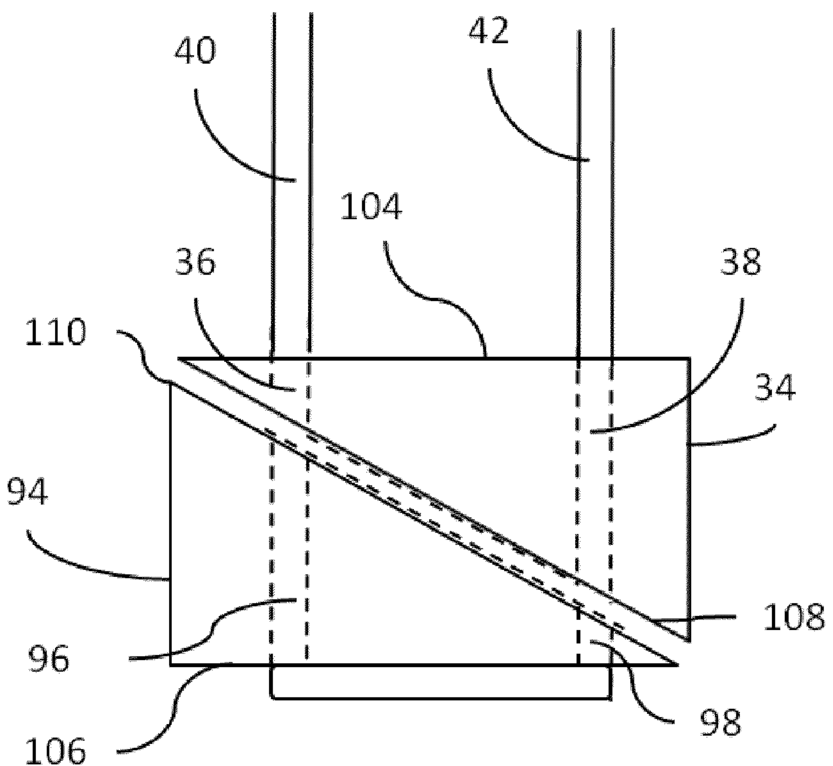
FIG. 7 shows a side-view depicting a suture anchor prior to deployment in accordance with an alternative preferred embodiment of the present invention.

FIGS. 6-7 show a top and side view of an alternate embodiment of suture anchor 20 prior to deployment. In this embodiment, suture anchor 20 has two sterile anchor segments 34 and 94. First sterile anchor segment 34 has a first hole 36 and a second hole 38. Second sterile anchor segment 94 has a third hole 96 and a fourth hole 98. First hole 36, and second hole 38 extend through first sterile anchor segment 34, and third hole 96 and fourth hole 98 extend through second sterile anchor segment 94. First 36, second 38, third 96 and fourth 98 holes are configured to permit suture 32 to pass through from one side of suture anchor 20 to the other. A distance 100 between first hole 36 and second hole 38 and a distance 102 between third hole 96 and fourth hole 98 are substantially equal. First suture segment 40 passes through first hole 36 and third hole 96 and second suture segment 42 passes through second hole 38 and fourth hole 98. Because distance 100 and distance 102 are substantially equal, when suture anchor 20 is deployed (discussed below), first hole 36 and third hole 96 become aligned and second hole 38 and fourth hole 98 become aligned.

In one embodiment, when first sterile anchor segment 34 and second sterile anchor segment 94 are positioned for insertion into bone 22 (FIG. 7), top surface 104 of first sterile anchor segment 34 and a bottom surface 106 of second sterile anchor segment 94 are substantially parallel. A bottom surface 108 of first sterile anchor segment 34 and a top surface 110 of second sterile anchor segment 94 may also be tapered. Tapering bottom surface 108 of first sterile anchor segment 34 and top surface 110 of second sterile anchor segment 94 encourages a rotation of second sterile anchor segment 94 upon deployment (discussed below).

Figure 8:
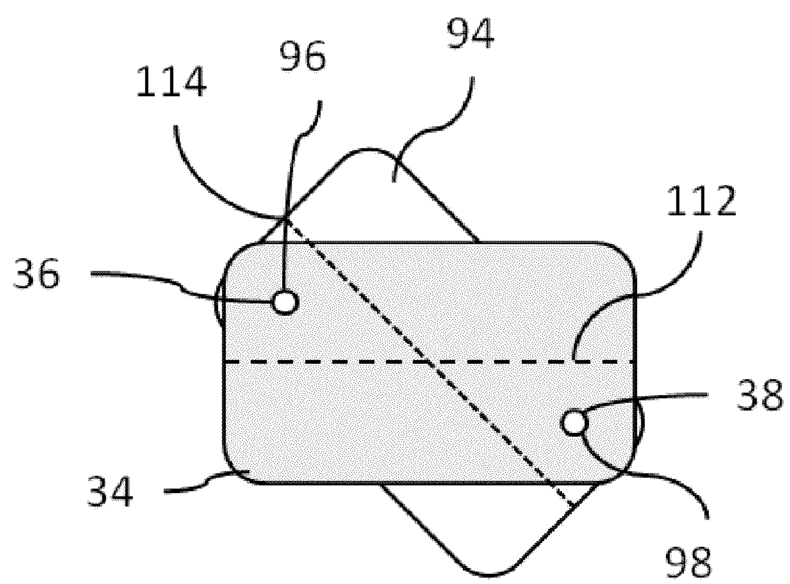
FIG. 8 shows a top-view depicting a suture anchor after deployment in accordance with an alternative preferred embodiment of the present invention.

FIG. 8 is a top-view of the alternate embodiment of suture anchor 20 shown in FIG. 6 after deployment. Once suture anchor 20 has been deployed within bone 22, and first suture segment 40 and second suture segment 42 have been pulled so that suture anchor 20 is adjacent to cortical bone 22' within spongy bone 22", first hole 36 and third hole 96 are aligned, and second hole 38 and fourth hole 98 are aligned. Thus, first suture segment 40 passes through first hole 36 and third hole 96 without any substantial folds or bends. Similarly, second suture segment 42 passes through second hole 38 and fourth hole 98 without any substantial folds or bends.

First sterile anchor segment 34 is centered around an axis 112. Second sterile anchor segment 94 is centered around an axis 1 14. Prior to deployment, axis 112 and axis 114 are aligned, as may be imagined by viewing FIG. 6. This alignment of axis 112 and axis 114 reduces the exposed surface area of suture anchor 20, and aids in reducing the size of hole 24 used to insert suture anchor 20. When deployed, pulling first suture segment 40 causes first hole 36 and third hole 96 to align. Pulling second suture segment 42 causes second hole 38 and fourth hole 98 to align. The alignment of holes 36, 38, 96, and 98 causes axis 114 of second sterile anchor segment 94 to rotate from axis 112 of first sterile anchor segment 34, as shown in FIG. 8. This rotation of axes increases the surface area of suture anchor 20, and provides a greater area inside spongy bone 22" upon which forces placed on suture anchor 20 can be distributed. One skilled in the art will recognize that although FIGS. 6-8 and the related descriptions discuss the use of two sterile suture segments, any number of sterile suture segments may be used to effect the distribution of force.

In summary, the present invention teaches a suture anchor 20 that is inserted within the spongy bone 22" and does not extend into cortical bone 22'. First suture segment 40 and second suture segment 42 extend from the suture anchor 20 and through cortical bone 22' through hole 24 drilled by a surgeon as part of the surgical procedure. Because suture segments 40 and 42 are the only aspect of suture anchor 20 that impede the healing of bone 22, the healing will be faster, and the healed bone 22 will be stronger.

Suture anchor 20 requires only one hole 24 in order to be installed. Suture anchor inserting device 58 passes through hole 24, and inserts suture anchor 20 into spongy bone 22". Thus, no additional incisions are necessary to access and position suture anchor 20.

As suture anchor 20 is not secured within bone 22, if additional surgeries to the same or proximal areas are necessary, suture segments 40 and 42 need only be cut, and a new hole can be drilled at the same or proximal area to where hole 24 was initially drilled.

Although the preferred embodiments of the invention have been illustrated and described in detail, it will be readily apparent to those skilled in the art that various modifications may be made therein without departing from the spirit of the invention or from the scope of the appended claims.

What is claimed is:

1. A method of using a suture anchor (20), said suture anchor (20) including a first anchor segment (34) and a second anchor segment (94), said first anchor segment (34) having a first hole (36), a second hole (38), and a bottom side (108), said second anchor segment (94) having a third hole (96), a fourth hole (98), and a top side (110), said top side (110) facing said bottom side (108), said first and second sterile anchor segments (34, 94) being physically separate elements that are coupled together via a first suture segment (40) passing through both of said first and third holes (36, 96) and a second suture segment (42) passing through both of said second and fourth holes (38, 98), and said method comprises:

forming a hole (24) in a bone (22), said bone (22) comprising a spongy bone (22") and a cortical bone (22');

inserting said suture anchor (20) through said hole (24) and within said spongy bone (22") such that said suture anchor (20) does not extend into said cortical bone (22'), wherein prior to said inserting operation, a first axis (112) of said first sterile suture segment (34) is aligned with a second axis (114) of said second sterile suture segment (94); and applying tension to said first suture segment (40) and said second suture segment (42) to position said suture anchor (20) such that said suture anchor (20) spans said hole (24) , wherein said applying operation causes said second sterile anchor segment (94) to rotate relative to said first sterile anchor segment (34) such that said first and second axes (112, 114) move out of alignment when said suture anchor (20) is deployed.

2. A method of using a suture anchor (20) as claimed in claim 1 wherein said inserting activity further comprises:

placing said suture anchor (20) in a suture anchor inserting device (58);

inserting said suture anchor inserting device (58) within said cortical bone (22') through said hole (24); and pushing said suture anchor (20) out of said suture anchor inserting device (58) such that no portion of said suture anchor (20) extends into said cortical bone (22').

3. A method of using a suture anchor (20) as claimed in claim 2 wherein said applying activity further comprises:

pulling said suture anchor (20) toward said suture anchor inserting device (58) such that said suture anchor (20) is offset from an axis (56) aligned with said hole (24); and extracting said suture anchor inserting device (58) such that said suture anchor (20) spans said hole (24).

4. A method of using a suture anchor (20) as claimed in claim 2 wherein said inserting activity further comprises:

holding said suture anchor (20) in a positioning unit (60); and pushing said suture anchor (20) from said positioning unit (60) into said bone (22) with a deployment device (62);

wherein said suture anchor (20) is aligned with an axis (92) when held in said positioning unit (60) and said deployment device (62) causes said suture anchor (20) to rotate from said axis (92).

5. A method of using a suture anchor (20) as claimed in claim 4 wherein said deployment device (62) is further configured to encourage said suture anchor (20) to rotate to a direction perpendicular to said axis (92).

* * * * *